United States Patent [19]

Bugaut et al.

[11] 4,152,112
[45] May 1, 1979

[54] DYEING COMPOSITION FOR KERATINIC FIBERS CONTAINING PARAPHENYLENEDIAMINES

[75] Inventors: Andrée Bugaut, Boulogne; Alain R. Genet, Neuilly Plaisance; Koovi G. Dossou, Vert-Galant par Vaujours, all of France

[73] Assignee: L'Oreal, Paris, France

[21] Appl. No.: 724,581

[22] Filed: Sep. 20, 1976

[30] Foreign Application Priority Data

Sep. 17, 1976 [FR] France ................................ 76 27957

[51] Int. Cl.$^2$ .............................................. A61K 7/13
[52] U.S. Cl. ........................................ 8/10.2; 8/11;
8/32; 260/553 A; 260/556 A; 260/558 A;
260/570.7; 260/575
[58] Field of Search ................................ 8/10.2, 11, 32;
260/553 A, 556 A, 558 A, 570.7 R, 575

[56] References Cited

U.S. PATENT DOCUMENTS

| | | | |
|---|---|---|---|
| 2,592,364 | 4/1952 | Weissberger et al. | 260/570.7 R |
| 3,037,057 | 5/1962 | Tinsley et al. | 260/578 |
| 3,642,769 | 2/1972 | Maritz et al. | 260/570.7 R |
| 3,697,215 | 10/1972 | Kalopissis et al. | 260/553 A |
| 3,711,546 | 1/1973 | Simon | 260/558 A |
| 3,820,948 | 6/1974 | Berth | 8/10.2 |
| 3,933,886 | 1/1976 | Saygin | 8/10.2 |

OTHER PUBLICATIONS

Chemical Abstracts, vol. 44, columns 9070–9071 (1950).

*Primary Examiner*—Bernard Helfin
*Assistant Examiner*—Vera C. Clarke
*Attorney, Agent, or Firm*—Brisebois & Kruger

[57] ABSTRACT

Dye compositions, especially for human hair containing the new chemical compounds of the general formula

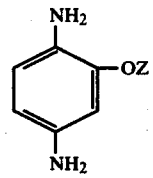

(I)

in which formula the radical Z is selected in the group formed by the hydroxyalkyl, alkoxyalkyl, acylaminoalkyl, carbalkoxyaminoalkyl, mesylaminoalkyl, ureidoalkyl, aminoalkyl, monoalkylaminoalkyl, dialkyl-aminoalkyl radicals, and the salts of the corresponding acids. Among the preferred acid salts, the sulfates, hydrochlorides, phosphates and tartrates may be mentioned.

This dye is particularly suited for use with a coupler of the formula

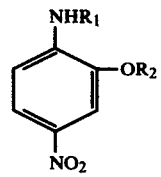

(II)

in which formula $R_3$ and $R_4$ are identical or different and may represent a hydrogen atom, alkoxy radical, or an alkyl radical and in which $R_5$ is a radical selected in the group formed by the acyl, carbalkoxy and ureido radicals.

12 Claims, No Drawings

DYEING COMPOSITION FOR KERATINIC FIBERS CONTAINING PARAPHENYLENEDIAMINES

In order to be selected at what is called an oxidation hair dye, the paraphenylenediamines must, on the one hand, have the advantage of good innocuousness, on the other hand impart to the hair, in an alkaline oxidizing medium, colorations having the qualities sought by the man skilled in the art. It is important, in particular, that they be able to impart by themselves to keratinic fibers, a sombre coloration called "deep coloration" such as chestnut, brown, grey or black, without which it would be difficult to formulate dyeing compositions leading to natural shades.

In association with compounds called couplers, judiciously selected, they may, moreover, make it possible to impart to the hair colorations rich in glints, shiny, having a sufficient chromaticity, and good stability to light, to inclement weather, and to shampooing.

The present invention has as its purpose to describe a category of new paraphenylenediamines which have all the advantages required so that the paraphenylenediamines may be selected as hair dyes.

The present invention has also for its purpose to describe the dyeing compositions using new paraphenyenediamines.

The present invention has for an object the new industrial product which consists of the new chemical compounds of the general formula

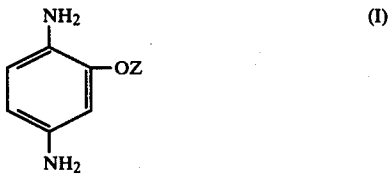

(I)

in which formula the radical Z is selected in the group formed by the hydroxyalkyl, alkoxyalkyl, acylaminoalkyl, carbalkoxyaminoalkyl, mesylaminoalkyl, ureidoalkyl, aminoalkyl, monoalkylaminoalkyl, dialkyl-aminoalkyl radicals, and the salts of the corresponding acids. Among the preferred acid salts, the sulfates, hydrochlorides, phosphates and tartrates may be mentioned.

The compound of formula (I) may easily be prepared by techniques known to the man skilled in the art utilizing as starting material a compound of the formula

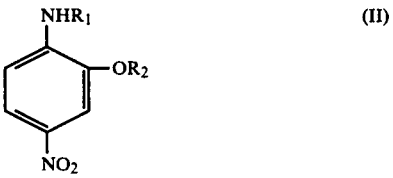

(II)

in which formula $R_1$ represents a hydrogen atom or a radical substituent and $R_2$ a radical substituent capable of giving rise, with or without intermediate transformation to the radical Z appearing in the formula of the compounds of formula (I). In particular, the radical $R_1$ may be an acetyl radical or a hydrogen atom. On this starting material of formula (II) one effectuates the reduction of the nitro group in $NH_2$.

The new chemical compounds of formula (I) are particularly usable in dyeing compositions for keratinic fibers. The present invention has thus also for an object a dyeing composition for keratinic fibers and particularly for human hair characterized by the fact that it contains in aqueous solution, at least one compound of formula (I).

In a preferred embodiment the composition according to the invention contains from 0.03 to 6% by weight of at least one compound of formula (I) in proportion to the total weight of the composition. The pH of the composition is advantageously selected in the range going from 8 to 11.5 and preferably is comprised between 9 and 10. Among the alkalizing agents which may be used, one may mention ammonia, alkylamines such as ethylamine or triethylamine, the alkanolamines such as the mono-, di-, or tri-ethanolamine, the ammonium derivatives, the hydroxides of sodium or potassium, the carbonates of sodium or potassium.

The dyeing compositions claimed may contain only, as coloring agents, one or more paraphenylenediamines of formula (I). The compounds of formula (I) are, in effect, particularly valuable for the sombre colorations which they are capable of imparting by themselves to the keratinic fibers in an alkaline oxidizing medium, particularly in the presence of hydrogen peroxide. Depending upon the particular formula of the compound of formula (I) used, depending upon the pH of the dyeing composition, the nature of the alkalizing agent, or even on the nature of the other constituents of the dyeing composition, the colorations obtained in the presence of hydrogen peroxide or concentrations in the compound of formula (I) comprise between 3 and 6% by weight, may vary from more or less sombre brown sometimes with reddish brown or violet glints, to blacks, often shaded with violet or blue. For concentrations going from 1 to 3% in the compound of formula (I) one obtains, in the presence of hydrogen peroxide colorations of keratinic fibers going from more or less burnt beiges to grey.

Thus the sombre colorations which are thus imparted to the keratinic fibers, in an oxidizing alkaline medium, by the compound according to the invention, constitute what the man skilled in the art calls the depth indispensable to obtaining natural shades in oxidation dyeing. It is thus clear that the dyeing qualities of this depth, to wit, shade and stability to light and to inclement weather play an important part in the value of the paraphenylenediamines as "oxidation bases" in hair dyeing. On this important point, the compounds of formula (I) are remarkable both for the aesthetic qualities of the shades obtained and for the stability of these shades in time, under light, and in inclement weather.

Moreover, certain compounds of formula (I), such as (2,5-diamino) phenoxyethanol are capable, in an alkaline medium, by simple oxidation in the air, without using any other oxidizing agent, to color the keratinic fibers grey. It follows that these compounds according to the invention, when they are associated in dyeing compounds with direct dyes such as nitrated dyes of the benzene series, have the advantage of permitting to confer to keratinic fibers without any supply of oxidizing agents, very bright, clear natural colors.

The compound of formula (I) may be used as oxidation bases in the presence of couplers such as metadiphenols, metaphenylenediamines, metaaminophenols, as well as couplers corresponding to the general formula

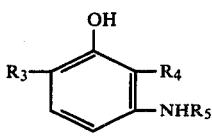

(III)

in which formula R₃ and R₄ are identical or different and may represent a hydrogen atom, alkoxy radical, or an alkyl radical and in which R₅ is a radical selected in the group formed by the acyl, carbalkoxy and ureido radicals. With the couplers above mentioned, the compounds of formula (I) lead, in an oxidizing alkaline medium, to the formation of colored indoanilines or indamines, which formation takes place in situ in the keratinic fiber during the oxidation dyeing.

It is desirable, of course, that the colorations imparted to the keratinic fibers by these indoanilines or these indamines, have a sufficient chromaticity and a good stability. Plus it has been found that the compounds of formula (I) applied to keratinic fibers in association with couplers of formula (III) impart to these fibers in an alkaline oxidizing medium very bright, more or less purple blue shades, having a surprising chromaticity and a very good stability to light and inclement weather. This is an important advantage of the compounds of formula (I) in view of the value which the contribution of a stable blue has in capillary formulation.

Moreover, certain compounds of formula (I) such as (2,5-diamino) phenoxyethanol, in association with the metaaminophenols such as 2-methyl-5-amino phenol, impart to the hair purple colorations of good stability.

The dyeing compositions according to the invention may also contain, in addition to the paraphenylenediamines of formula (I) other products such as those above indicated, taken singly or in combination:

1. Other oxidation bases and, in particular, either the paraphenylenediamines such as paraphenylenediamine, 2,6-dimethyl-3-methoxy paraphenylenediamine, 4-amino-N-β-methoxyethyl aniline, 4-amino-N,N-di-β-hydroxyethyl aniline, or the paraaminophenols such as paraaminophenol, 2-methyl-4-amino phenol, 3-chloro-4-amino phenol;
2. The leucoderivatives of indoanilines and indophenols such as 4,4'-dihydroxy-2-amino-5-methyl diphenylamine, the 4-4'-dihydroxy-2-amino-N-hydroxyethyl-5-methyl-2'-chloro diphenylamine, 2,4'-diamino-4-hydroxy-5-methyl diphenylamine;
3. The polyaminophenols, the monoaminodiphenols, the diaminodiphenols, the polyphenols such as trihydroxybenzene;
4. The direct dyes and, in particular, direct dyes of the benzene series such as 1-amino-N,N-di-hydroxyethyl-3-nitro-4-amino-N'-methyl benzene; the 1-amino-N,N-methyl-β-hydroxyethyl-3-nitro-4-amino-N'-β-hydroxyethyl benzene, 1-amino-N,N-methyl-β-hydroxyethyl-3-nitro-4-amino-N'-methyl benzene, 3-nitro-4-amino-N-β-amino-hydroxyethyl anisole, 3-nitro-4-amino-N-β-hydroxyethyl phenol, (3-nitro-4-amino) phenoxyethanol, (3-nitro-4-amino-N-methyl) phenoxyethanol, 2-β-hydroxyethylamino-5-nitro anisole, 2-methyl-4-nitro aniline and 2-nitro-5-amino phenol;
5. Various usual additives such as penetrating agents, foaming agents, thickening agents, antioxidizing agents, alkalizing agents, perfumes, sequestrating agents, and film forming products.

One may also add to the composition according to the invention hydrosoluble, anionic, cationic, non ionic, or amphoteric surface-active agents. Among the surface-active agents particularly usable one may mention the alkylbenzene-sulfonates, the alkylnaphthalene-sulfonates, the sulfates, ethersulfate and sulfonates of fatty alcohols, the quaternary ammonium salts such as triethylcetylammonium bromide, cetyl-pyridinium bromide, the diethanolamides of fatty acids, the acids and polyoxyethylenated alcohols and polyoxyethylenated alkylphenols. Preferably, the surface-active agents are present in the composition according to the invention in a proportion comprised between 0.5 and 30% by weight and preferably between 4 and 25% by weight. One may also add to the composition according to the invention organic solvents to solubilize the compounds which are not sufficiently soluble in water. Among the solvents which may advantageously be used one may mention by way of example ethanol, isopropanol, glycerin, glycols such as butyl-glycol, ethylene-glycol, propylene-glycol, the monoethylether and monomethylether and diethylene-glycol and analogous products. The solvents may advantageously be present in the composition in a proportion going from 1 to 40% by weight and preferably comprised between 5 and 30% by weight.

The thickening products which may be added to the composition according to the invention may advantageously be taken from the group formed by sodium alginate, gum arabic, the cellulose derivatives such as methylcellulose, hydroxyethylcellulose, hydroxypropyl-methylcellulose, sodium salt of carboxymethylcellulose and the polymers of acrylic acid. One may also use mineral thickening agents such as bentonite. Preferably, the thickening agents are present in a proportion comprised between 0.5 and 5% by weight in proportion to the total composition and preferably between 0.5 and 3% by weight.

The anti-oxidizing agents which may be added to the composition according to the invention may be taken in the group formed by sodium sulfite, thioglycolic acid, the acid sulfite of sodium, ascorbic acid, and hydroquinone. These anti-oxidizing agents may be present in the composition in a proportion comprised between 0.05 and 1% in proportion to the total weight of the composition.

The dyeing composition according to the invention may take the form of a liquid solution, a paste, a cream, a gel, or any other form appropriate to carry out a dyeing of keratinic fibers.

In order that the object of the invention may be better understood one will now describe, by way of purely illustrative and non-limiting examples, the preparation of six compounds of formula (I) and the use of these compounds in dyeing compositions according to the invention.

EXAMPLE 1: Preparation of dihydrochloride of (2,5-diamino) phenoxyethanol

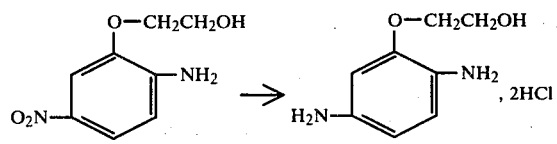

One brings to reflux, under agitation, 100 ml of a hydroalcoholic solution (93% ethanol, 7% H₂O) to which 65 g of zinc powder and 4 grams of ammonium chloride have been added; then one adds, little by little, 0.126 mol (25 g) of (3-nitro-6-amino) phenoxyethanol (product described in French Pat. No. 74-36651).

When the addition is terminated, one maintains the reflux for 10 minutes then one filters the boiling reaction mixture while recovering the filtrate in a vial under vacuum containing 32 ml of 36% hydrochloric acid chilled in a ice bath.

By cooling the filtrate the dihydrochloride of (2,5-diamino) phenoxyethanol crystallizes.

The product is drained, washed with a little absolute alcohol, and vacuum dried.

The product has the following characteristics:
Molecular weight calculated for $C_8H_{14}O_2N_2Cl_2$—241
Molecular weight found by potentiometric analysis with the aid of an N/10 soda solution—240

The analysis of the product gives the following results:

| Analysis | Calculated for $C_8H_{14}O_2N_2Cl_2$ | Found |
|---|---|---|
| C % | 39.83 | 39.72 |
| H % | 5.80 | 5.98 |
| N % | 11.62 | 11.84 |
| Cl % | 29.46 | 29.37 |

EXAMPLE 2: Preparation of dihydrochloride of (2,5-diamino) phenyl, β-methoxyethylether

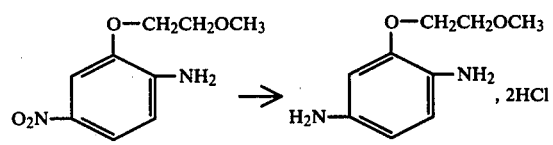

One brings to reflux under agitation, 250 ml of hydroalcoholic solution (93% ethanol, 7% $H_2O$) to which 82 g of zinc powder and 5 g of ammonium chloride have been added; then one adds, little by little, 0.165 mol (35 g) of (3-nitro-6-amino) phenyl, β-methoxyethylether (product described in French Pat. No. 76-12985).

When the addition is completed, one maintains the reflux for 30 minutes then one filters the boiling reaction mixture while recovering the filtrate in a vial under vacuum containing 80 ml of 36% hydrochloric acid cooled in an ice bath.

By cooling the filtrate, the dihydrochloride of (2,5-diamino) phenyl, β-methoxyethylether precipitates in crystalized form.

It is drained, washed with iced absolute alcohol, recrystallized in alcohol at 96° and vacuum dried at 60° C.

The product obtained has the following characteristics:
Molecular mass calculated for $C_9H_{16}N_2O_2Cl_2$—255
Molecular weight found by potentiometric analysis with the aid of an N/10 soda solution—250

The analysis of the product obtained gives the following results:

| Analysis | Calculated for $C_9H_{16}N_2O_2Cl_2$ | Found |
|---|---|---|
| C % | 42.35 | 42.44 |
| H % | 6.27 | 6.58 |
| N % | 10.98 | 10.99 |
| Cl % | 27.84 | 27.67 |

EXAMPLE 3: Preparation of dihydrochloride, monohydroxide of (2,5-diamino) phenyl, β-mesylaminoethylether.

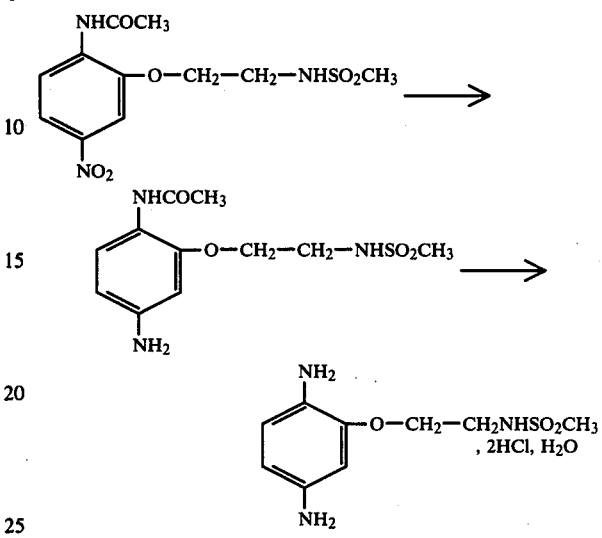

First step: Preparation of (2-acetylamino-5-amino) phenyl, β-mesylaminoethylether.

One adds, little by little, under agitation, 0.006 mol (2 g) of (3-nitro-6-acetylamino) phenyl, β-mesylaminoethylether [product described in French application No. 76-12985] in 10 ml of a hydroalcoholic solution (50% ethanol, 50% water), to which 0.2 g of ammonium chloride and 4 grams of zinc powder have been added and first brought to reflux.

The addition completed, one maintains the reaction mixture at reflux for 10 minutes and then filters it boiling.

By cooling the filtrate, (2-acetylamino-5-amino) phenyl, β-mesylaminoethylether crystallizes.

The product is drained, washed with the minimum of iced hydroalcoholic solution and vacuum dried. It melts at 105° C.

Second step: Preparation of dihydrochloride, monohydroxide of (2,5-diamino) phenyl, β-mesylaminoethylether.

One dissolves 0.04 mol. (11.5 g) of (2-acetylamino-5-amino) phenyl, β-mesylaminoethylether in 30 ml of 35% hydrochloric acid which has been previously heated in a boiling water bath. One maintains the heating in the boiling water bath for 30 minutes.

By cooling the hydrochloric solution the dihydrochloride of (2,5-diamino) phenyl, β-mesylaminoethylether crystallizes.

The product is drained, washed with a little iced hydrochloric acid and vacuum dried at 50° C.

The analysis of the product obtained gives the following results:

| Analysis | Calculated for $C_9H_{15}N_3O_3S, 2HCl, H_2O$ | Found |
|---|---|---|
| C % | 32.15 | 32.05 |
| H % | 5.69 | 5.50 |
| N % | 12.50 | 12.72 |
| Cl % | 21.46 | 21.67 |
| S % | 9.42 | 9.47 |

EXAMPLE 4: Preparation of dihydrochloride of (2,5-diamino) phenyl, β-ureidoethylether.

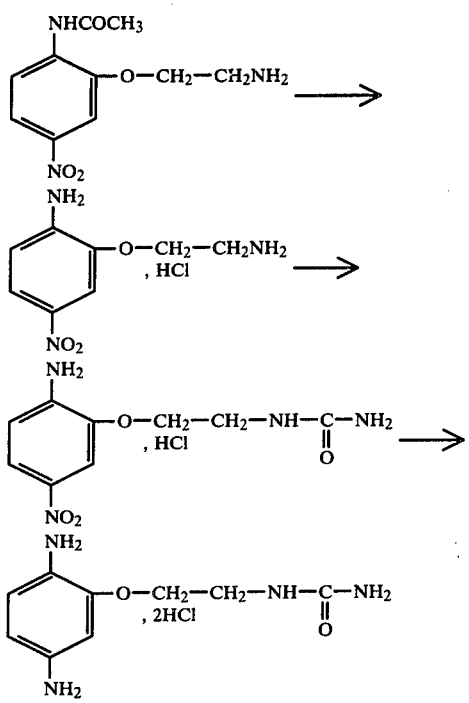

First step: Preparation of monohydrochloride of (3-nitro-6-amino) phenyl, β-aminoethylether.

One heats for 5 hours in a boiling water bath 0.02 mol (4.78 g) of (3-nitro-6-acetylamino) phenyl, β-aminoethylether (product described in French application No. 76-12985) in 15 ml of 35% hydrochloric acid.

After cooling the hydrochloric solution, dilution with water and neutralization with ammonia, one drains the monohydrochloride of (3-nitro-6-amino) phenyl, β-aminoethylether, which precipitates in crystallized form.

The product is washed with a little iced alcohol and vacuum dried.

Analysis of the product obtained gives the following results:

| Analysis | Calculated for $C_8H_{12}N_3O_3Cl$ | Found |
|---|---|---|
| C % | 41.12 | 41.14 |
| H % | 5.18 | 5.14 |
| N % | 17.98 | 18.14 |
| Cl % | 15.17 | 15.27 |

Second step: Preparation of (3-nitro-6-amino) phenyl, β-ureidoethylether.

To 0.072 mol (16.8 g) of monohydrochloride of (3-nitro-6-amino) phenyl, β-aminoethylether in suspension in 110 ml of water, one adds, under good agitation, 0.086 mol (7.1 g) of 98% potassium isocyanate in solution and 36 ml of water. The reaction medium is heated under agitation for an hour at 50° C. and then left overnight at ambient temperature.

The product formed is drained, washed in water, and vacuum dried. After recrystallization in an alcohol/acetone solution and vacuum drying it melts at 219° C.

Analysis of the product obtained gives the following results:

| Analysis | Calculated for $C_9H_{12}N_4O_4$ | Found |
|---|---|---|
| C % | 45.00 | 44.95 |
| H % | 5.04 | 5.15 |
| N % | 23.33 | 23.11 |

Third step: Preparation of dihydrochloride of (2,5-diamino) phenyl, β-ureidoethylether.

One brings to reflux, under agitation, 10 ml of ethanol at 96° to which 1 ml of water, 0.2 g of ammonium chloride and 5 g of zinc powder have been added.

Then one adds, little by little, 0.008 mol (2 g) of (3-nitro-6-amino) phenyl, β-ureidoethylether.

The addition terminated, one maintains the heating for 10 minutes, then the reaction mixture is filtered while boiling and recovering the filtrate in a vial under vacuum containing 2.1 ml of 36% chilled hydrochloric acid in an ice bath.

By cooling the filtrate the dihydrochloride of (2,5-diamino) phenyl, β-ureidoethylether crystallizes. It is drained, recrystallized in alcohol at 80° and vacuum dried at 60° C. The dihydrochloride crystallizes with a molecule of ethanol. The analysis of the product obtained gives the following results:

| Analysis | Calculated for $C_9H_{16}O_2N_4Cl_2, C_2H_5OH$ | Found |
|---|---|---|
| Cl % | 21.54 | 21.69 |
| N % | 17.02 | 17.34 |

EXAMPLE 5: Preparation of dihydrochloride of (2,5-diamino) phenyl, β-acetylaminoethylether.

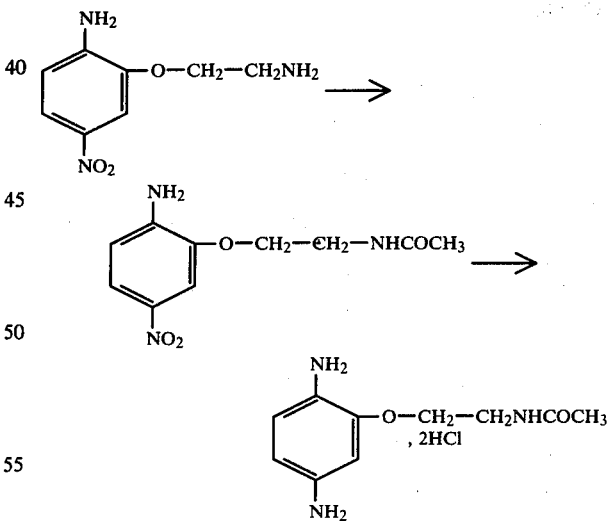

First step: Preparation of (3-nitro-6-amino) phenyl, β-acetylaminoethylether.

Beginning with the hydrochloride of (3-nitro-6-amino) phenyl, β-aminoethylether prepared in example 4, one easily releases, by treatment with an aqueous soda solution (3-nitro-6-amino) phenyl, β-aminoethylether (melting point: 129° C.).

The characteristics of the product obtained are the following:

Molecular weight calculated for $C_8H_{11}N_3O_3$—197

Molecular weight found by potentiometric analysis in acetic acid with an N/10 solution of perchloric acid—199

To 0.30 mol (6 g) of (3-nitro-6-amino) phenyl, β-acetylaminoethylether partially in solution in 30 ml of dioxane at 40° C., one adds, under agitation, 0.031 mol (3 ml) of acetic anhydride. Agitation is continued for an hour at ambient temperature.

The expected product is crystallized.

It is drained, washed with a little isopropanol and vacuum dried at 80° C. It melts at 139° C.

The analysis of the obtained product gives the following results:

| Analysis | Calculated for $C_{10}H_{13}N_3O_4$ | Found |
|---|---|---|
| C % | 50.20 | 50.14 |
| H % | 5.48 | 5.57 |
| N % | 17.57 | 17.38 |

Second step: Preparation of dihydrochloride of (2,5-diamino) phenyl, β-acetylaminoethylether.

One brings to reflux, under agitation, 10 ml of ethanol at 96° to which one has added 1 ml of water, 0.2 g of ammonium chloride and 5 g of zinc powder. One adds 0.01 mol (2.4 g) of (3-nitro-6-amino) phenyl, β-acetylaminoethylether. One maintains the reflux for 15 minutes then the boiling reaction mixture is filtered while collecting the filtrate in 2.1 ml of 36% hydrochloric acid.

While cooling the filtrate the expected product crystallizes. It is drained and vacuum dried at 100° C.

The characteristics of the product obtained are the following:
Molecular weight calculated for $C_{10}H_{15}N_3O_2$, 2HCl—282
Molecular weight found by potentiometric analysis in water using a N/10 soda solution—284

The analysis of the product obtained gives the following results:

| Analysis | Calculated for $C_{10}H_{15}N_3O_2.2HCl$ | Found |
|---|---|---|
| C % | 42.56 | 42.37 |
| H % | 6.07 | 6.24 |
| N % | 14.89 | 14.72 |
| Cl % | 25.13 | 25.10 |

EXAMPLE 6: Preparation of trihydrochloride of (2,5-diamino) phenyl, β-aminoethylether.

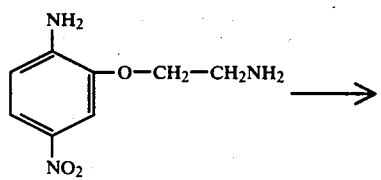

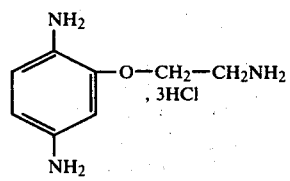

One brings to reflux, under agitation, 10 ml of ethanol, 1 ml of water to which 0.2 g of ammonium chloride and 5 g of zinc powder have been added. One adds 0.01 mol (1.97 g) of (3-nitro-6-amino) phenyl, β-aminoethylether.

One maintains the reflux for 10 minutes then filters the boiling reacting medium while collecting the filtrate in 3.1 mols of 36% hydrochloric acid. By cooling the filtrate the expected trihydrochloride crystallizes. It is drained, washed with a little iced alcohol and vacuum dried at 80° C.

The characteristics of the product obtained are the following:
Molecular weight calculated for $C_8H_{13}N_3O,3$ HCl—276.5
Molecular weight found by potentiometric analysis in water with the aid of an N/10 soda solution—281

EXAMPLE 7:

The following dyeing composition is prepared:

| | |
|---|---|
| Compound of example 1 | 4 g |
| Sodium lauryl sulfate with 19% of oxyethylenated starting alcohol | 20 g |
| Ethylene diaminotetracetic acid | 0.2 g |
| Ammonia at 22° B. | 1 g |
| Water, q.s. | 100 g |

The pH is equal to 10. At the moment of use, 100 g of hydrogen peroxide at 20 volumes is added.

This solution applied for 30 minutes at 25° C. to bleached hair imparts thereto, after rinsing and shampooing, a very deep chestnut having bronze glints.

EXAMPLE 8:

The following dyeing composition is prepared:

| | |
|---|---|
| Compound of example 2 | 4 g |
| Oleic alcohol oxyethylenated with 2 mols of ethylene oxide | 4.5 g |
| Oleic alcohol oxyethylenated with 4 mols of ethylene oxide | 4.5 g |
| Laurylamine oxyethylenated with 12 mols of ethylene oxide | 4.5 g |
| Diethanolamides of fatty acids of copra | 9 g |
| Monopropyleneglycol | 3.6 g |
| Butylglycol | 8 g |
| Ethanol | 6 g |
| 40% sodium bisulfite | 1 g |
| Ammonia at 22° B. | 10 g |
| Water, q.s. | 100 g |

The pH is 9.3. At the moment of use, 100 g of hydrogen peroxide at 20 volumes is added.

This mixture applied for 30 minutes at 25° C. to bleached hair imparts thereto, after rinsing and shampooing, a coffee color.

EXAMPLE 9:

The following dyeing composition is prepared:

| | |
|---|---|
| Compound of example 1 | 4.5 g |
| Butylglycol | 4.5 g |
| Lauric alcohol oxyethylenated with 10.5 mols of ethylene oxide | 4.5 g |
| Triethanolamine | 10 g |
| Water, q.s. | 100 g |

The pH is 8.

This mixture applied directly for 30 minutes to bleached hair imparts thereto, after rinsing and shampooing, a clear, metallic grey shade.

EXAMPLE 10:

The following dyeing composition is prepared:

| | |
|---|---|
| Compound of example 3 | 3 g |
| Butylglycol | 4.5 g |
| Lauric alcohol oxyethylenated at 10.5 mols of ethylene oxide | 4.5 g |
| Ammonia at 22° B. | 10 g |
| Water, q.s. | 100 g |

The pH is 10. At the moment of use, 100 g of hydrogen peroxide is added.

This mixture applied to bleached hair for 20 minutes at 25° C. imparts thereto, after rinsing and shampooing, a turtle dove grey coloration.

EXAMPLE 11:

The following dyeing composition is prepared:

| | |
|---|---|
| Compound of example 1 | 4 g |
| Butylglycol | 4.5 g |
| Lauric alcohol oxyethylenated with 10.5 mols of ethylene oxide | 4.5 g |
| Triethanolamine | 10 g |
| Water, q.s. | 100 g |

The pH is 8. At the moment of use 100 g of hydrogen peroxide at 20 volumes is added.

This mixture applied for 30 minutes at 25° C. to bleached hair imparts thereto, after rinsing and shampooing, a blackish brown color with violet glints.

EXAMPLE 12:

The following dyeing composition is prepared:

| | |
|---|---|
| Compound of example 1 | 4 g |
| Trihydroxybenzene | 0.85 g |
| Butylglycol | 4.5 g |
| Lauric alcohol oxyethylenated with 10.5 mols of ethylene oxide | 4.5 g |
| Triethanolamine | 10 g |
| Water, q.s. | 100 g |

The pH is equal to 8. At the moment of use, 100 g of hydrogen peroxide at 20 volumes is added.

This solution applied for 30 minutes at 25° C. to bleached hair imparts thereto, after rinsing and shampooing, an anthracite black coloration.

EXAMPLE 13:

The following dyeing composition is prepared:

| | |
|---|---|
| Compound of example 1 | 4.5 g |
| 3-nitro-4-amino-N-methyl phenoxyethanol | 0.12 g |
| Butylglycol | 4.5 g |
| Lauric alcohol oxyethylenated with 10.5 mols of ethylene oxide | 4.5 g |
| Ammonia at 22° B. | 10 g |
| Water, q.s. | 100 g |

The pH is 9.5.

This solution applied directly for 30 minutes at 25° C. to bleached hair imparts thereto, after rinsing and shampooing, a golden beige coloration.

EXAMPLE 14:

The following dyeing composition is prepared:

| | |
|---|---|
| Compound of example 4 | 3.5 g |
| Sodium lauryl sulfate with 19% of oxyethylenated starting alcohol | 20 g |
| Ethylene diaminotetraacetic acid | 0.2 g |
| Ammonia at 22° B. | 10 g |
| 40% sodium bisulfite | 1 g |
| Water, q.s. | 100 g. |

The pH is 10. At the moment of use one adds 100 g of hydrogen peroxide at 20 volumes.

This mixture applied for 30 minutes at 25° C. to bleached hair imparts thereto, after rinsing and shampooing, a clear bronze coloration.

EXAMPLE 15:

The following dyeing composition is prepared:

| | |
|---|---|
| Compound of example 2 | 0.4 g |
| 2-methyl-5-ureido phenol | 0.26 g |
| 3-nitro-4-amino-N-$\beta$-hydroxyethyl anisole | 0.075 g |
| Butylglycol | 10 g |
| Diethanolamides of fatty acids of copra | 8.2 g |
| Ammonia at 22° B. | 8 g |
| Water, q.s. | 100 g |

The pH is equal to 10.2. At the moment of use, 100 g of hydrogen peroxide at 20 volumes is added.

This mixture applied for 20 minutes at ambient temperature to bleached hair imparts thereto, after rinsing and shampooing, a bluish silver grey coloration.

EXAMPLE 16:

The following dyeing composition is prepared:

| | |
|---|---|
| Compound of example 1 | 0.603 g |
| 2-methoxy-5-acetylamino phenol | 0.453 g |
| Sodium lauryl sulfate with 19% of oxyethylenated starting alcohol | 20 g |
| Ethylene diaminotetraacetic acid | 0.2 g |
| Ammonia at 22° B. | 10 g |
| 40% sodium bisulfite | 1 g |
| Water, q.s. | 100 g |

The pH is equal to 11. At the moment of use, 100 grams of hydrogen peroxide at 20 volumes are added.

This mixture applied for 20 minutes at 25° C. to 95% naturally white hair imparts thereto, after rinsing and shampooing a lavender blue coloration.

EXAMPLE 17:

The following dyeing composition is prepared:

| | |
|---|---|
| Compound of example 2 | 2.5 g |
| 2-methoxy-5-carbethoxyamino phenol | 1.7 g |
| Butylglycol | 15 g |
| Diethanolamides of fatty acids of copra | 7.5 g |
| Ammonia at 22° B. | 10 g |
| Water, q.s. | 100 g |

The pH is equal to 10. At the moment of use, 80 g of hydrogen peroxide at 20 volumes is added.

This mixture applied for 20 minutes at 25° C. to bleached hair imparts thereto, after rinsing and shampooing, a strong violet blue coloration.

EXAMPLE 18:

The following dyeing composition is prepared:

| | |
|---|---|
| Compound of example 2 | 0.765 g |

-continued

| | |
|---|---|
| 5-methylureido phenol | 0.166 g |
| Butylglycol | 15 g |
| Polymer of acrylic acid (M.W = 2 to 3 millions) sold under the commercial name "Carbopol 934" by Goodrich Chemical Company | 3.37 g |
| Water, q.s. | 100 g |
| Ammonia at 22° B. | 10 g |

The pH is equal to 9. At the moment of use, 75 g of hydrogen peroxide at 20 volumes is added.

This mixture applied for 30 minutes at ambient temperature to bleached hair imparts thereto, after rinsing and shampooing, a metallic grey coloration.

EXAMPLE 19:

The following dyeing composition is prepared:

| | |
|---|---|
| Compound of example 1 | 0.15 g |
| 2-methyl-5-ureido phenol | 0.136 g |
| 3-nitro-4-amino-N-β-hydroxyethyl anisole | 0.125 g |
| Butylglycol | 15 g |
| Polymer of acrylic acid (M.W = 2 to 3 millions) sold under commercial name "Carbopol 934" by the Goodrich Chemical Co. | 3.5 g |
| Ammonia at 22° B. | 8 g |
| Water, q.s. | 100 g |

The pH is equal to 8.4. At the moment of use, 40 g of hydrogen peroxide at 20 volumes is added.

This mixture applied to bleached hair for 20 minutes at 25° C. imparts thereto, after rinsing and shampooing, a rosewood color.

EXAMPLE 20:

The following dyeing composition is prepared:

| | |
|---|---|
| Compound of example 3 | 0.35 g |
| 2,6-dimethyl-5-acetylamino phenol | 0.197 g |
| 3-nitro-4-amino-N-β-hydroxyethyl phenol | 0.20 g |
| 2-nitro-5-amino phenol | 0.20 g |
| Oleic alcohol oxyethylenated with 2 mols of ethylene oxide | 4.5 g |
| Oleic alcohol oxyethylenated with 4 mols of ethylene oxide | 9 g |
| Propyleneglycol | 10 g |
| Ammonia at 22° B. | 10 g |
| Water, q.s. | 100 g |

The pH is equal to 10.5. At the moment of use, 100 g of hydrogen peroxide at 20 volumes is added.

This mixture applied for 15 minutes at 25° C. to bleached hair imparts thereto, after rinsing and shampooing, a golden black coloration.

EXAMPLE 21:

The following dyeing composition is prepared:

| | |
|---|---|
| Compound of example 3 | 5 g |
| 3-nitro-4-amino-N-β-hydroxyethyl anisole | 0.2 g |
| Monomethyl ester of diethyleneglycol | 9 g |
| Ammonia at 22° B. | 10 g |
| Water, q.s. | 100 g |

The pH is equal to 9.5. At the moment of use, 100 g of hydrogen peroxide at 20 volumes is added.

This mixture applied for 30 minutes at 25° C. to 95% naturally white hair imparts thereto, after rinsing and shampooing, a deep golden chestnut coloration.

EXAMPLE 22:

The following dyeing composition is prepared:

| | |
|---|---|
| Compound of example 3 | 0.6 g |
| 2-methyl-5-ureido phenol | 0.314 g |
| 3-nitro-4-amino-N-β-hydroxyethyl phenol | 0.04 g |
| 3-nitro-6-amino-N-β-hydroxyethyl anisole | 0.1 g |
| Butylglycol | 10 g |
| Nonylphenol having 4 mols of ethylene oxide | 17.6 g |
| Nonylphenol having 9 mols of ethylene oxide | 17.6 g |
| Ammonia at 22° B. | 2 g |
| Water, q.s. | 100 g |

The pH is equal to 9.7. At the moment of use, 100 g of hydrogen peroxide at 20 volumes is added.

This mixture applied for 20 minutes at ambient temperature to bleached hair imparts thereto, after rinsing and shampooing, a clear silver coloration.

EXAMPLE 23

The following dyeing composition is prepared:

| | |
|---|---|
| Compound of example 3 | 0.318 g |
| 2,6-dimethyl-5-acetylamino phenol | 0.179 g |
| 2,4'-diamino-4-hydroxy-5-methyl diphenylamine | 0.25 g |
| (3-nitro-6-amino) phenoxyethanol | 0.075 g |
| Oleic alcohol oxyethylenated with 2 mols of ethylene oxide | 4.65 g |
| Oleic alcohol oxyethylenated with 4 mols of ethylene oxide | 9.3 g |
| Propyleneglycol | 9.5 g |
| Ammonia at 22° B. | 7 g |
| Water, q.s. | 100 g |

The pH is equal to 10.3. At the moment of use, 100 g of hydrogen peroxide at 20 volumes is added.

This mixture applied for 20 minutes at ambient temperature to bleached hair imparts thereto, after rinsing and shampooing, a deep burnt beige coloration with violet glints.

EXAMPLE 24

The following dyeing composition is prepared:

| | |
|---|---|
| Compound of example 1 | 0.06 g |
| Compound of example 3 | 0.06 g |
| 2-methoxy-5-carbethoxyamino phenol | 0.16 g |
| 2-methyl-5-amino phenol | 0.1 g |
| Paraaminophenol | 0.15 g |
| Dihydrochloride of paraphenylenediamine | 0.05 g |
| 2-amino-N-β-hydroxyethyl-5-nitro anisole | 0.03 g |
| Alcohol at 96° | 10 g |
| Diethanolamides of fatty acids of copra | 8.5 g |
| Ammonia at 22° B. | 5 g |
| Water, q.s. | 100 g |

The pH is 10.4. At the moment of use 85 g of hydrogen peroxide at 20 volumes is added.

This mixture applied for 20 minutes at 25° C. to bleached hair imparts thereto, after rinsing and shampooing, a clear, copper red chestnut coloration.

EXAMPLE 25

The following dyeing composition is prepared:

| | |
|---|---|
| Compound of example 2 | 0.15 g |
| 4-amino-N,N-di-β-hydroxyethyl aniline sulfate | 0.18 g |
| Paraaminophenol | 0.20 g |
| 2-methoxy-5-carbethoxyamino phenol | 0.33 g |
| (3-nitro-4-amino-N-methyl) phenoxyethanol | 0.1 g |
| Butylglycol | 7 g |

-continued

| | |
|---|---|
| Nonylphenol having 4 mols of ethylene oxide | 18 g |
| Nonylphenol having 9 mols of ethylene oxide | 18 g |
| Ammonia at 22° B. | 5 g |
| Water, q.s. | 100 g |

The pH is equal to 10.3. At the moment of use 50 g of hydrogen peroxide at 20 volumes is added.

This mixture applied for 20 minutes at 25° C. to bleached hair imparts thereto, after rinsing and shampooing, a mauve silver grey coloration.

EXAMPLE 26

The following dyeing composition is prepared:

| | |
|---|---|
| Compound of example 1 | 1 g |
| 2-methyl-5-ureido phenol | 0.05 g |
| 2,6-dimethyl-5-acetylamino phenol | 0.05 g |
| 4,4'-dihydroxy-2-amino-N-$\beta$-hydroxyethyl 5-methyl-2'-chloro diphenylamine | 0.5 g |
| Dihydrochloride of 2,6-diamino hydroquinone | 0.5 g |
| Trihydrochloride of 2,6-diamino-4-amino-N,N-diethyl phenol | 0.20 g |
| 3-nitro-4-amino-N-$\beta$-hydroxyethyl anisole | 0.35 g |
| Diethanolamides of fatty acids of copra | 10 g |
| Ammonia at 22° B. | 5 g |
| Water, q.s. | 100 g |

The pH is equal to 10. At the moment of use, 40 g of hydrogen peroxide at 20 volumes is added.

This mixture is applied to bleached hair for 25 minutes at 25° C. After rinsing and shampooing, a deep maroon coloration with violet glints is obtained.

EXAMPLE 27

The following dyeing composition is prepared:

| | |
|---|---|
| Compound of example 4 | 0.82 g |
| 2-methoxy-5-carbethoxyamino phenol | 0.53 g |
| Oleic alcohol oxyethylenated with 2 mols of ethylene oxide | 4.5 g |
| Oleic alcohol oxyethylenated with 4 mols of ethylene oxide | 4.5 g |
| Diethanolamides of fatty acids of copra | 9 g |
| Laurylamine oxyethylenated with 12 mols of ethylene oxide | 4.5 g |
| Monopropyleneglycol | 3.6 g |
| Butylglycol | 8 g |
| Ethanol | 5.4 g |
| 40% sodium bisulfite | 1 g |
| Ammonia at 22° B. | 10 g |
| Water, q.s. | 100 g |

The pH is equal to 9.5. At the moment of use, 100 g of hydrogen peroxide at 20 volumes is added.

This mixture applied for 25 minutes at 25° C. to bleached hair imparts thereto, an extremely shiny mauve shade.

EXAMPLE 28

The following dyeing composition is prepared:

| | |
|---|---|
| Compound of example 1 | 0.6 g |
| 2-methyl-5-carbethoxyamino phenol | 0.3 g |
| 1-amino-N,N-dihydroxyethyl-3-nitro-4-amino-N'-methyl benzene | 0.3 g |
| 4,4'-dihydroxy-2-amino-5-methyl diphenylamine | 0.5 g |
| Butylglycol | 10 g |
| Nonylphenol having 4 mols of ethylene oxide | 16 g |
| Nonylphenol having 9 mols of ethylene oxide | 16 g |
| Ammonia at 22° B. | 10 g |
| Water, q.s. | $\phi$g |

The pH is 10.4. At the moment of use, 85 g of hydrogen peroxide at 20 volumes is added.

This mixture applied for 30 minutes at 25° C. to bleached hair imparts thereto, after rinsing and shampooing a slightly rosy nacreous beige shade.

EXAMPLE 29

The following dyeing composition is prepared:

| | |
|---|---|
| Compound of example 2 | 3 g |
| 3-nitro-4-amino-N-methyl phenoxyethanol | 0.1 g |
| 1-amino-N,N-methyl-$\beta$-hydroxyethyl-3-nitro-4-amino-N'-methyl benzene | 0.05 g |
| 1-amino-N,N-di-$\beta$-hydroxyethyl-3-nitro-4-amino-N'-methyl benzene | 0.02 g |
| Butylglycol | 4.5 g |
| Lauric alcohol oxyethylenated at 10.5 mols of ethylene oxide | 4.5 g |
| Ammonia at 22° B. | 10 g |
| Water, q.s. | 100 g |

The pH is equal to 10. At the moment of use, one adds 100 g of hydrogen peroxide at 20 volumes.

This solution applied for 30 minutes at 25° C. to bleached hair imparts thereto, after rinsing and shampooing, a beaver color.

EXAMPLE 30

The following dyeing composition is prepared:

| | |
|---|---|
| Compound of example 6 | 0.69 g |
| 2-methoxy-5-acetylamino phenol | 0.45 g |
| Sodium lauryl sulfate with 19% of oxyethylenated starting alcohol | 20 g |
| Ethylene diaminotetraacetic acid | 0.2 g |
| Ammonia at 22° B. | 10 g |
| 40% sodium bisulfite | 1 g |
| Water, q.s. | 100 g |

The pH is 10.3. At the moment of use, 100 g of hydrogen peroxide at 100 volumes is added.

This mixture applied for 20 minutes at 25° C. to bleached hair imparts thereto, after rinsing and shampooing, a strong pure blue shade.

EXAMPLE 31

The following dyeing composition is prepared:

| | |
|---|---|
| Compound of example 5 | 0.84 g |
| 2-methoxy-5-carbethoxyamino phenol | 0.45 g |
| Sodium lauryl sulfate with 19% of oxyethylenated starting alcohol | 11 20 g |
| Ethylene diaminotetraacetic acid | 0.2 g |
| Ammonia at 22° B. | 10 g |
| 40% sodium bisulfite | 1 g |
| Water, q.s. | 100 g |

The pH is 10.3. At the moment of use, 100 g of hydrogen peroxide at 20 volumes is added.

This mixture applied for 20 minutes at ambient temperature to bleached hair imparts thereto, after rinsing and shampooing an extremely strong and shiny violet blue coloration.

EXAMPLE 32

The following dyeing composition is prepared:

| | |
|---|---|
| Compound of example 6 | 4 g |
| Butylglycol | 5 g |
| Lauric alcohol oxyethylenated at 10.5 mols of ethylene oxide | 5 g |

| | |
|---|---|
| Ammonia at 22° B. | 10 g |
| Water, q.s. | 100 g |

The pH is 9. At the moment of use 100 g of hydrogen peroxide at 20 volumes is added.

This composition applied for 30 minutes at 25° C. to naturally white hair imparts thereto, after rinsing and shampooing, a very sombre marine blue coloration:

EXAMPLE 33

The following dyeing composition is prepared:

| | |
|---|---|
| Compound of example 5 | 4 g |
| Butylglycol | 5 g |
| Lauric alcohol oxyethylenated with 10.5 mols of ethylene oxide | 5 g |
| Ammonia at 22° B. | 10 g |
| Water, q.s. | 100 g |

The pH is 9.8. At the moment of use, 100 g of hydrogen peroxide at 20 volumes is added.

This mixture applied for 30 minutes at 25° C. to bleached hair imparts thereto, after rinsing and shampooing, a deep burnt chestnut coloration.

We claim:

1. A dyeing composition for keratinic fibers and particularly for human hair, that contains, in aqueous solution a dyeing amount of at least one paraphenylenediamine compound having the general formula

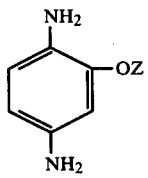

in which Z is selected from the group consisting of hydroxyalkyl, alkoxyalkyl, acylaminoalkyl, mesylaminoalkyl, ureidoalkyl, aminoalkyl, and the corresponding acid salts, and at the moment of application at least one oxidizing agent selected from the group consisting of hydrogen peroxide, urea peroxide and the persalts.

2. The composition of claim 1 in which the paraphenylenediamine compound is in the form of acid salts selected from the group consisting of sulfates, hydrochlorides, phosphates, and tartrates.

3. The composition of claim 1 which contains 0.03 to 6% by weight of at least one compound of formula (I) in proportion to the total weight of the composition.

4. The composition of claim 1 having a pH between 8 and 11.5.

5. The composition of claim 4, which also contains an alkalizing agent selected from the group consisting of ammonia, alkylamines alkanolamines, hydroxides of sodium and potassium and carbonates of sodium and potassium.

6. The composition of claim 1, which also contains at least one direct dye.

7. The composition of claim 6, in which the direct dyes are selected from the group consisting of 1-amino-N,N-dihydroxyethyl-3-nitro-4-amino-N'-methyl benzene, 1-amino-N,N-methyl-β-hydroxyethyl-3-nitro-4-amino-N'-β-hydroxyethyl benzene, 1-amino-N,N-methyl-β-hydroxyethyl-3-nitro-4-amino-N'-methyl benzene, 3-nitro-4-amino-N-β-hydroxyethyl anisole, 3-nitro-4-amino-N-β-hydroxyethyl phenol, (3-nitro-4-amino) phenoxyethanol, (3-nitro-4-amino-N-methyl) phenoxyethanol, 2-β-hydroxyethylamino-5-nitro anisole, 2-methyl-4-nitro aniline and 2-nitro-5-amino phenol.

8. The composition of claim 1, which also contains at least one coupler selected from the group consisting of metadiphenols, metaphenylenediamines, metaaminophenols, and couplers of the general formula

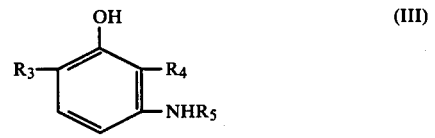

in which $R_3$ and $R_4$ are identical or different and may represent hydrogen, alkoxy or alkyl, and in which $R_5$ is selected from the group consisting of acyl, carbalkoxy and ureido.

9. The composition of claim 1, which also contains at least one oxidation base other than the compound of formula (I).

10. The composition of claim 9, which contains as a supplementary oxidation base not corresponding to the compound of formula (I) at least one paraphenylenediamine.

11. The composition of claim 9, which contains, as a supplementary oxidation base not corresponding to the compound of formula (I), at least one paraaminophenol.

12. The composition of claim 1, which also contains at least one product selected from the group consisting of:
 1.—the leucoderivatives of indoanilines and indophenols; and
 2.—the polyaminophenols, the monoaminodiphenols, the diaminodiphenols, the polyphenols.

* * * * *